United States Patent
Takebe et al.

(10) Patent No.: US 10,668,108 B2
(45) Date of Patent: Jun. 2, 2020

(54) COMPOSITIONS AND METHODS OF TREATING LIVER DISEASE

(71) Applicant: Children's Hospital Medical Center, Cincinnati, OH (US)

(72) Inventors: Takanori Takebe, Cincinnati, OH (US); Rie Ouchi, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 16/343,157

(22) PCT Filed: Nov. 3, 2017

(86) PCT No.: PCT/US2017/059865
§ 371 (c)(1),
(2) Date: Apr. 18, 2019

(87) PCT Pub. No.: WO2018/085623
PCT Pub. Date: May 11, 2018

(65) Prior Publication Data
US 2019/0314387 A1  Oct. 17, 2019

Related U.S. Application Data

(60) Provisional application No. 62/517,525, filed on Jun. 9, 2017, provisional application No. 62/417,371, filed on Nov. 4, 2016.

(51) Int. Cl.
| | | |
|---|---|---|
| A61K 35/407 | (2015.01) | |
| A61P 1/16 | (2006.01) | |
| A61K 31/575 | (2006.01) | |
| A61K 45/06 | (2006.01) | |
| C12N 5/071 | (2010.01) | |
| C12N 5/074 | (2010.01) | |
| C12N 15/01 | (2006.01) | |
| A61K 9/00 | (2006.01) | |

(52) U.S. Cl.
CPC .......... A61K 35/407 (2013.01); A61K 9/0029 (2013.01); A61K 31/575 (2013.01); A61P 1/16 (2018.01); C12N 5/0671 (2013.01); C12N 5/0696 (2013.01); C12N 15/01 (2013.01); A61K 45/06 (2013.01); C12N 2501/119 (2013.01); C12N 2506/45 (2013.01)

(58) Field of Classification Search
CPC .. A61K 31/407; A61K 9/0029; A61K 31/575; A61K 45/05; C12N 5/0671; C12N 5/0696
USPC ....................................................... 514/169
See application file for complete search history.

(56) References Cited

U.S. PATENT DOCUMENTS

| | | |
|---|---|---|
| 7,326,572 B2 | 2/2008 | Fisk et al. |
| 7,510,876 B2 | 3/2009 | D'Amour et al. |
| 9,381,181 B2 | 7/2016 | Roberts et al. |
| 9,616,039 B2 | 4/2017 | Roberts et al. |
| 9,719,068 B2 | 8/2017 | Wells et al. |
| 9,732,116 B2 | 8/2017 | Steiner et al. |
| 9,763,964 B2 | 9/2017 | Pellicciari et al. |
| 9,765,301 B2 | 9/2017 | Ortega et al. |
| 9,849,104 B2 | 12/2017 | Bisgaier et al. |
| 10,045,977 B2 | 8/2018 | Wu et al. |
| 10,052,337 B2 | 8/2018 | Lancaster et al. |
| 10,174,289 B2 | 1/2019 | Wells et al. |
| 10,301,303 B2 | 5/2019 | Liu |
| 2012/0071451 A1 | 3/2012 | Spenard et al. |
| 2016/0177270 A1 | 6/2016 | Takebe et al. |
| 2016/0237400 A1 | 8/2016 | Xian |
| 2016/0245653 A1 | 8/2016 | Park et al. |
| 2016/0263098 A1 | 9/2016 | Mantzoros |
| 2017/0239262 A1 | 8/2017 | Lefebvre |
| 2017/0319548 A1 | 11/2017 | Lefebvre |
| 2018/0021341 A1 | 1/2018 | Harriman et al. |

FOREIGN PATENT DOCUMENTS

| | | | |
|---|---|---|---|
| CN | 105985395 A | 10/2016 | |
| EP | 2 393 917 B1 | 12/2011 | |
| EP | 3228306 A1 | 10/2017 | |
| WO | WO 2010/090513 A2 | 8/2010 | |
| WO | WO 2010/094694 A1 | 8/2010 | |
| WO | WO 2015/183920 A2 | 12/2015 | |
| WO | WO 2015/185714 A1 | 12/2015 | |
| WO | WO-2016164413 A1 * | 10/2016 | ........... A61K 31/575 |
| WO | WO 2016/176208 A1 | 11/2016 | |
| WO | WO 2017/04193 A1 | 3/2017 | |
| WO | WO 2017/048322 A1 | 3/2017 | |

(Continued)

OTHER PUBLICATIONS

Ajmera, V., et al., "Novel Plasma Biomarkers Associated with Liver Disease Severity in Adults with Nonalcoholic Fatty Liver Disease," Hepatology, 2017, 65(1):65-77, 21 pgs.

(Continued)

*Primary Examiner* — Yevgeny Valenrod

(74) *Attorney, Agent, or Firm* — Frost Brown Todd LLC; Nicole M. Tepe

(57) ABSTRACT

Disclosed are methods of treating or reducing the occurrence of a steatohepatitis disorder. The disorder may include, for example, NASH, parenteral nutrition associated liver disease (PNALD), or genetic forms of liver disease. The method may comprise the step of administering a composition comprising obeticholic acid to an individual in need thereof.

8 Claims, 2 Drawing Sheets

(56) References Cited

FOREIGN PATENT DOCUMENTS

| WO | WO 2017/066659 A1 | 4/2017 |
|----|-------------------|--------|
| WO | WO 2017/153992 A1 | 9/2017 |
| WO | WO 2017/184586 A1 | 10/2017 |

OTHER PUBLICATIONS

Aleo, M.D., et al., "Human Drug-Induced Liver Injury Severity is Highly Associated with Dual Inhibition of Liver Mitochondrial Function and Bile Salt Export Pump," Hepatology, 2014, 60:1015-1022, 8 pgs.
Andrews, et al., "Embryonic stem (ES) cells and embryonal carcinoma (EC) cells: opposite sides of the same coin," Biochem Soc Trans, 2005, 339(part 6):1526-1530, 5 pgs.
Ang, et al., "The formation and maintenance of the definitive endoderm lineage in the mouse: involvement of HNF3/forkhead proteins," Development, 1993, 119:1301-1315, 15 pgs.
Asai, A., et al. "Paracrine signals regulate human liver organoid maturation from induced pluripotent stem cells," Development, 2017, 144: 1056-1064, 30 pgs.
Bahar Halpern, K., et al. "Single-cell spatial reconstruction reveals global division of labour in the mammalian liver," Nature, 2017, 542:352-356, 18 pgs.
Barth, C.A., et al., "Transcellular transport of fluorescein in hapatocyte monolayers: Evidence for functional polarity of cells in cultue," Proc Natl Acad Sci USA, 1982, 79:4985-4987, 3 pgs.
Begriche, K., et al., "Drug-induced toxicity on mitochondria and lipid metabolism: Mechanistic diversity and deleterious consequences for the liver," J Hepatol, 2011, 54:773-794, 22 pgs.
Bell, L.N., et al., "Epidemiology of Idiosyncratic Drug-Induced Liver Injury," Semin Liver Dis, 2009, 29(4):337-347, 11 pgs.
Bernardi, P., "The permeability transition pore. Control points of a cyclosporin A-sensitive mitochondrial channel involved in cell death," Biochim Biophys Acta, 1996, 1275:5-9, 5 pgs.
Bohan, T.P., et al., "Effect of L-carnitine treatment for valproate-induced hepatotoxicity," Neurology, 2001, 56:1405-1409, 5 pgs.
Boullata, J.I., et al. "A.S.P.E.N. Clinical Guidelines: Parental Nutrition Ordering, Order Review, Compounding, Labeling, and Dispensing," J Parenter Enteral Nutr, 2014, 38(3):334-377, 44 pgs.
Bravo, P., et al., "Efficient In Vitro Vectorial Transport of a Fluorescent Conjugated Bile Acid Analogue by Polarized Hepatic Hybrid WIF-B and WIF-B9 Cells," Hepatology, 1998, 27:576-583, 8 pgs.
Browning, J.D., et al., "Molecular mediators of hepati steatosis and liver injury," J Clin Invest, 2004, 114(2):147-152, 6 pgs.
Cabezas, J., et al., "Nonalcoholic Fatty Liver Disease: A Pathological View," Chapter 8, in *Liver Biopsy—Indications, Procedures Results*, N. Tagaya (Ed.), InTechOpen, Nov. 21, 2012, pp. 161-188, 28 pgs., ISBN 978-953-51-0853-5.
Chang, J.H., et al., "Evaluating the In Vitro Inhibition of UGT1A1, OATP1B1, OATP1B3, MRP2, and BSEP in Predicting Drug-Induced Hyperbilirubinemia," Mol Pharm, 2013, 10:3067-3075, 9 pgs.
Chatterjee, S., et al., "Hepatocyte-based in vitro model for assessment of drug-induced cholestasis," Toxicol Appl Pharmacol, 2014, 274:124-136, 13 pgs.
Chen, Y., et al., "Retinoic acid signaling is essential for pancreas development and promotes indocrine at the expense of exocrine cell differentiation in *Xenopus*," Dev Biol, 2004, 271:144-160, 17 pgs.
Chughlay, M.F., et al., "N-acetylcysteine for non-paracetamol drug-induced liver injury: a systematic review," Br J Clin Pharmacol, 2016, 81:1021-1029, 9 pgs.
Cutrin, J.C., et al., "Reperfusion Damage to the Bile Canaliculi in Transplanted Human Liver," Hepatology, 1996, 24: 1053-1057, 5 pgs.
D'Amour, K.A., et al., "Efficient differentiation of human embryonic stem cells to definitive endoderm," Nature Biotechnology, 2005, 23(12):1534-1541, 8 pgs.

Dash, A., et al., "Pharmacotoxicology of clinically-relevant concentrations of obeticholic acid in an organotypic human hepatocyte system" Toxicol In Vitro, 2017, 39:93-103, 11 pgs.
Davidson, M.D., et al., "Long-term exposure to abnormal glucose levels alters drug metabolism pathways and insulin sensitivity in primary human hepatocytes," Sci Rep, 2016, 6:28178, 11 pgs.
De Santa Barbara, P., et al., "Development and differentiation of the intestinal epithelium," Cell Mol Life Sci, 2003, 60(7):1322-1332, 11 pgs
Dessimoz, J., et al., "FGF signaling is necessary for establishing gut tube domains along the anterior-posterior axis in vivo," Mech Dev, 2006, 123:42-55, 14 pgs.
Dumortier, G., et al., "Tolérance hépatique des antipsychotiques atypiques, [Hepatic tolerance of atypical antipsychotic drugs]," L'Encéphale, 200, 28(1):542-551, 10 pgs.
Dvir-Ginzberg, M., et al., "Liver Tissue Engineering Within Alginate Scaffolds: Effects of Cell-Seeding Density on Hepatocyte Viability, Morphology, and Function," Tissue Eng, 2003, 9(4):757-766, 10 pgs.
Edling, Y., et al., "Increased sensitivity for troglitazone-induced cytotoxicity using a human in vitro co-culture model," Toxicol In Vitro, 2009, 23:1387-1395, 9 pgs.
El Kasmi, K.C., et al., "Phytosterols Promote Liver Injury and Kupffer Cell Activation in Parenteral Nutrition-Associated Disease," Sci Transl Med, 2013, 5(206):206ra137, 10 pgs.
El Taghdouini, A., et al., "In vitro reversion of activated primary human hepatic stellate cells," Fibrogenesis & Tissue Repair, 2015, 8:14, 15 pgs.
The Encode Project Consortium, "An integrated encyclopedia of DNA elements in the human genome," Nature, 2012, 489:57-74, 18 pgs.
Evans, M.J. et al., "Establishment in culture of pluripotent cells from mouse embryos," Nature, 1981, 292(5819):154-156, 3 pgs.
Fahrmayr, C., et al., "Phase I and II metabolism and MRP2-mediated export of bosentan in a MDCKII-OATP1B1-CYP3A4-UGT1A1-MRP2 quadruple-transfected cell line," Br J Pharmacol, 2013, 169:21-33, 13 pgs.
Falasca, L., et al., "The effect of retinoic acid on the re-establishment of differentiated hepatocyte phenotype in primary culture," Cell Tissue Res, 1998, 293:337-347, 11 pgs.
Fisher, A., et al., "Entacapone-Induced Hepatotoxicity and Hepatic Dysfunction," Mov Disord, 2002, 17:1362-1365, 4 pgs.
Fromenty, B., "Drug-induced liver injury in obesity," J Hepatol, 2013, 58:824-826, 3 pgs.
Geerts, A., et al., "Formation of Normal Desmin Intermediate Filaments in Mouse Hepatic Stellate Cells Requires Vimentin," Hepatology, 2001, 33:177-188, 12 pgs.
Gori, M., et al., "Investigating Nonalcoholic Fatty Liver Disease in a Liver-on-a-Chip Microfluidic Device," PLoS One, Jul. 2016, 11(7):e0159729, 15 pgs.
Hassan, W., et al., "Reduced Oxidative Stress Contributes to the Lipid Lowering Effects of Isoquercitrin in Free Fatty Acids Induced Hepatocytes," Oxid Med Cell Longev, 2014, 313602, 18 pgs.
Heidari, R., et al., "Factors affecting drug-induced liver injury: antithyroid drugs as instances," Clin Mol Hepatol, 2014, 20:237-248, 12 pgs.
Hynds, R.E., et al., "The relevance of human stem cell-derived organoid models for epithelial translational medicine," Stem Cells, 2013, 31(3):417-422, 11 pgs.
Ijpenberg, A., et al., "Wt1 and retinoic acid signaling are essential for stellate cell development and liver morphogenesis," Dev Biol, 2007, 312:157-170, 14 pgs.
Inoue, H., et al., "iPS cells: a game changer for future medicine," EMBO J, 2014, 33(5):409-417, 9 pgs.
Ito, K., et al., "Temporal Transition of Mechanical Characteristics of HUVEC/MSC Spheroids Using a Microfluidic Chip with Force Sensor Probes," Micromachines, 2016, 7:221, 14 pgs.
Jalan-Sakrikar, N., et al., "Hedgehog Signaling Overcomes an EZH2-Dependent Epigenetic Barrier to Promote Cholangiocyte Expansion," PLoS One, 2016, 11(12):e0168266, 19 pgs.
Kaji, K., et al., "Virus free induction of pluripotency and subsequent excision of reprogramming factors," Nature, 2009, 458(7239):771-775, 10 pgs.

(56) References Cited

OTHER PUBLICATIONS

Kanuri, G., et al., "In Vitro and in Vivo Models of Non-Alcoholic Fatty Liver Disease (NAFLD)," Int J Mol Sci, 2013, 14:11963-11980, 18 pgs.
Kelly, G.M., et al., "Retinoic Acid and the Development of the Endoderm," J Dev Biol, 2015, 3:25-56, 32 pgs.
Klimanskaya, I., et al. "Human embryonic stem cells derived without feeder cells," Lancet, 2005, 365(9471):1636-1641, 6 pgs.
Kock, K., et al., "A Perspective on Efflux Transport Proteins in the Liver," Clin Pharmacol Ther, 2012, 92(5):599-612, 29 pgs.
Koehler, E.M., et al., "Presence of Diabetes Mellitus and Steatosis is Associated With Liver Stiffness in a General Population: The Rotterdam Study," Hepatology, 2016, 63:138-147, 10 pgs.
Kordes, C., et al., "Hepatic stellate cells contribute to progenitor cells and liver reeneration," J Clin Invest, 2014, 124(12):5503-5515, 13 pgs.
Krähenbühl, S., et al., "Toxicity of Bile Acids on the Electron Transport Chain of Isolated Rat Liver Mitochondria," Hepatology, 1994, 19:471-479, 9 pgs.
Kubo, A., et al., "Development of definitive endoderm from embryonic stem cells in culture," Development, 2004, 131(7):1651-1662, 12 pgs.
Kullak-Ublick, G.A., et al., "Drug induced liver injury: recent advantages in diagnosis and risk assessment," Gut, 2017, 66:1154-1164, 11 pgs.
Kumar, J.A., et al., "Controversies in the Mechanism of Total Parenteral Nutrition Induced Pathology," Children, 2015, 2:358-370, 13 pgs.
Lancaster, M.A., et al., "Organogenesis in a dish: Modeling development and disease using organoid technologies," Science, 2014, 345(6194):1247125-1-1247125-9, 9 pgs.
Lê, S., et al., "FactoMineR: An R Package for Multivariate Analysis," Journal of Statistical Software, 2008, 25(1):1-18, 18 pgs.
Le Vee, M., et al., "Polarized expresssion of drug transporters in differentiated human hepatoma HepaRG cells," Toxicol In Vitro, 2013, 27:1979-1986, 8 pgs.
Lechner, C., et al., "Development of a fluorescence-based assay for drug interactions with human Multidrug Resistance Related Protein (MRP2; ABCC2) in MDCKII-MRP2 membranes vesicles," Eur J Pharm Biopharm, 2010, 75:284-290, 7 pgs.
Lee, W.M., et al., "Intravenous N-Acetylcysteine Improves Transplant-Free Survival in Early Stage Non-Acetaminophen Acute Liver Failure," Gastroenterology, 2009, 137(3):856-864, 18 pgs.
Leslie, E.M., et al., "Differential Inhibition of Rat and Human Na$^+$-Dependent Taurocholate Cotransporting Polypeptide (NTCP/SLC10A1)by Bosentan: A Mechanism for Species Differenced in Hepatotocity," J Pharmacol Exp Ther, 2007, 321(3):1170-1178, 9 pgs.
Li, N., et al., "A Systematic Assessment of Mitochondrial Function Identified Novel Signatures for Drug-Induced Mitochondrial Disruption in Cells," Toxicol Sci, 2014, 142(1):261-273, 13 pgs.
Makin, A.J., et al., "A 7-Year Experience of Severe Acetaminophen-Induced Hepatotoxicity (1987-1993)," Gastroenterology, 1995, 109:1907-1916, 10 pgs.
Malinen, M.M., et al., "Differentiation of liver progenitor cell line to functional organotypic cultures in 3D nanofibrillar cellolose and hyaluronan-gelatin hydrogels," Biomaterials, 2014, 35:5110-5121, 12 pgs.
Marcum, Z.A., et al., "Medication Adherence to Multi-Drug Regimens," Clin Geriatr Med, 2012, 28(2):287-300, 15 pgs.
Markova, S.M., et al., "Association of CYP2C9*2 With Bosentan-Induced Liver Injury," Clin Pharmacol Ther., Dec. 2013, 94(6):678-86, 9 pgs.
Martin, G.R., "Teratocarcinomas and Mammalian Embryogenesis," Science, 1980, 209(4458):768-776, 9 pgs.
McCracken, K. W., et al., "Wnt/β-catenin promotes gastric fundus specifications in mice and humans," Nature, 2017, 541(7636):182-187, 31 pgs.

McLin, V.A., et al., "Repression of Wnt/β-canenin signaling in the anterior endoderm is essential for liver and pancreas development," Development, 2007, 134:2207-2217, 11 pgs.
Mercaldi, C.J., et al., "Methods to Identify and Compare Parenteral Nutrition Administered From Hospital-Compound and Premixed Multichamber Bags in a Retrospetive Hospital Claims Database," J Parenter Enteral Nutr, 2012, 36(3):330-336, 7 pgs.
Michaut, A., et al., "A cellular model to study drug-induced liver injury in nonalcoholic fatty liver disease: application of acetaminophen," Toxicol Appl Pharmacol, 2016, 292:40-55, 35 pgs.
Miki, T., et al., "Hepatic Differentiation of Human Embryonic Stem Cells Is Promoted by Three-Dimensional Dynamic Perfusion Culture Conditions," Tissue Eng: Part C Methods, 2011, 17(5):557-568, 12 pgs.
Mörk, L.M., et a., "Comparison Culture Media for Bile Acid Transport Studies in Primary Human Hepatocytes," J Clin Exp Hepatol, 2012, 2:315-355, 8 pgs.
Nandivada, P., et al., "Treatment of Parenteral Nutrition-Associated Liver Disease: The Role of Lipid Emulsions$^{1-3}$," Nutr, Nov. 2013, 4:711-717, 7 pgs.
Navarro, V.J., et al., "Drug-Related Hepatotoxity," N Engl Med, 2006, 354:731-739, 9 pgs.
Negishi, T., et al., "Retinoic Acid Signaling Positively Regulates Liver Specification by Inducing wnt2bb Gene Expression in Medaka," Hepatology, 2010, 51:1037-1045, 9 pgs.
Neuschwander-Tetri, B.A., et al., "Farnesoid X nuclear receptor ligand obeticholic acid for non-cirrhotic, non-alcoholic steatophepatitis (FLINT): a multicentre, radomised, placebo-controlled trial," Lancet, 2015, 385, 956-965, 10 pgs.
Ni, X., et al. "Functional human induced hepatocytes (hiHeps) with bile acid synthesis and transport capcitis: A novel in vitro cholestatic model," Sci Rep, 2016, 6:38694, 16 pgs.
Nishida, T., et al., "Rat liver canalicular membrane vesicles contain an ATP-dependent bile acis transport system," Proc Natl Acad Sci USA, 1991, 88:6590-6594, 5 pgs.
Okita, K., et al., "Generation of Mouse Induced Pluripotent Stem Cells Without Viral Vectors," Science, 2008, 322(5903):949-953, 5 pgs.
Oorts, M., et al., "Drug-induced cholestasis risk assessment in sandwich-cultured human hepatocytes," Toxicol In Vitro, 2016, 34:179-186, 8 pgs.
Orso, G., et al., "Pediatric parenteral nutrition-associated liver disease and cholestasis: Novel advances in pathomechanisms-based prevention and treatment," Dig Liver Dis, 2016, 48:215-222, 8 pgs.
Park, H.R., et al., "Lipotoxicity of Palmitic Acid on Neural Progenitor Cells and Hippocampal Neurogeneis," Toxicological Research, Jun. 2011, 27(2):103-110, 8 pgs.
Pessayre, D., "Central role of mitochondria in drug-induced liver injury," Drug Metab Rev, 2012, 44(1):34-87, 54 pgs.
Pessayre, D., et al., "Mitochondrial involvement in drug-induced liver injury," in *Adverse Drug Reaction*, J. Uetrecht (ed.), Handb Exp Pharmacol 196, Springer-Verlag, Berling, Germany, 2010, pp. 311-365, 55 pgs.
Polson, J., et al., "AASLD Position Paper: The Management of Acute Liver Failure," Hepatology, 2005, 41(5):1179-1197, 19 pgs.
Purton, L.E., et al., "All-trans retinoic acid enhances the long-term repopulating activity of cultured hematopoietic stem cells," Blood, 2000, 95:470-477, 8 pgs.
Rachek, L.I., et al., "Troglitazone, but not rosiglitazone, damages mitochondrial DNA and induces mitochondrial dysfunction and cell death in human hepatocytes," Toxicol Appl Pharmacol, 2009, 240(3):348-354, 17 pgs.
Ramanchandran, S.D., et al., "In Vitro Generation of Functional Liver Organoid-Like Structures Using Adult Human Cells," PloS One, Oct. 2015, 10(10):1-14, 14 pgs.
Rector, R.S., et al., "Mitochondrial dysfunction precedes insulin resistance and hepatic steatosis and contributes to the natural history of non-alcoholic fatty liver disease in an obese rodent model," J Hepatol, 2010, 52(5):727-736, 20 pgs.
Reuben, A., et al. "Drug-Induced Acute Liver Failure: Results of a U.S. Multicenter, Prospective Study," Hepatology, 2010, 52:2065-2076, 12 pgs.

(56) References Cited

OTHER PUBLICATIONS

Ronn, R.E., et al., "Retinoic Acid Regulates Hematopoietic Development from Human Pluripotent Stem Cells," Stem Cell Reports, 2015, 4:269-281, 13 pgs.
Russo, M.W., et al., "Liver Transplantation for Acute Liver Failure From Drug Induced Liver Injury in the United States," Liver Transpl, 2004, 10:1018-1023, 6 pgs.
Saini, A., "Cystic Fibrosis Patients Benefit from Mini Guts," Cell Stem Cell, 2016, 19:425-427, 3 pgs.
Serviddio, G., et al., "Ursodeoxycholic Acid Protects Against Secondary Biliary Cirrhosis in Rats by Preventing Mitochondrial Oxidative Stress," Hepatology, 2004, 39:711-720, 10 pgs.
Si-Tayeb, K., et al., "Highly Efficient Generation of Human Hepatocyte-Like Cell from Induced Pluripoent Stem Cells," Hepatology, 2010, 51:297-305, 9 pgs.
Sloan, C.A., et al., "ENCODE data at the ENCODE portal," Nucleic Acids Res, 2016, 44:D726-D732, 7 pgs.
Sneddon, I.N., "The Relation Between Load and Penetration in the Axisymmetric Boussinesq Problem for a Punch of Arbitrary Profile," Int. J. Engng. Sci., 1965, 3:47-57, 11 pgs.
Song, W., et al., "Engraftment of human induced pluripotent stem cell-derived hepatocytes in immunocompetent mice via 3D co-aggregation and encapsulation," Sci Rep, 2015, 5:16884, 13 pgs.
Song, Z., et al., "Efficient generation of hepatocyte-like cells from human induced pluripotent stem cells," Cell Res, 2009, 19:1233-1241, 10 pgs.
Spence, J.R., et al., "Directed differentiation of human pluripotent stem cells into intestinal tissue in vitro," Nature, 2011, 470(7332):105-109, 13 pgs.
Stadtfeld, M., et al., "Induced pluripotent stem cells generated with viral integration," Science, 2008, 322(5903):945-949, 12 pgs.
Stafford, D., et al., "A conserved role for retinoid signaling in vertebrate pancreas development," Dev Genes Evol, 2004, 214:432-441, 10 pgs.
Stender, S., et al., "Adiposity Amplifies the Genetic Risk of Fatty Liver Disease Conferred by Multiple Loci," Nat Genet, 2017, 49(6):842-847, 18 pgs.
Stevens, J.L., et al., "The future of drug safety testing: expanding the view and narrowing the focus," Drug Discov Today, 2009, 14(3/4):162-167, 6 pgs.
Takahashi, K., et al., "Induction of Pluripotent Stem Cells from Adult Human Fibroblasts by Defined Factors," Cell, 2007, 131:861-872, 12 pgs.
Takebe, T., et al., "Human iPSC-Derived Miniature Organs: A Tool for Drug Studies," Clin Pharmacol Ther, 2014, 96(3):310-313, 4 pgs.
Takebe, T., et al., "Vascularized and Complex Organ Buds from Diverse Tissues via Mesenchymal Cell-Driven Condensation," Cell Stem Cell, 2015, 16:556-565, 10 pgs.
Takebe, T., et al., "Vascularized and functional human liver from an iPSC-derived organ bud transplant," Nature, 2013, 499:481-484, 5 pgs.
Takebe, T., et al., "Generation of a vasularized and functional human liver from an iPSC-derived organ bud transplant," Nat Protoc, 2014, 9(2):396-409, 14 pgs.
Thomson, et al. "Embryonic Stem Cell Lines Derived from Human Blastocysts," Science, 1998, 282(5391):1145-1148, 3 pgs.
Tian, X., et al., "Modulation of Multidrug Resistance-Associated Protein 2 (Mrp2) and Mrp3 Expression and Function with Small Interferring RNA in Sandwich-Cultured Rat Hepatocytes," Mol Pharmacol, 2004, 66(4):1004-1010, 7 pgs.
Troy, D.B. (ed.), Remington: The Science and Practice of Pharmacy, 21$^{st}$ Ed., 2006, Lippincott, Williams & Wilkens, Baltimore, MD, 6 pgs., Table of Contents Only.
Tsedensodnom, O., et al. "ROS: Redux and Paradox in Fatty Liver Disease," Hepatology, 2013, 58(4):1210-1212, 3 pgs.
Tsukada, N., et al., "The Structure and Organization of the Bile Canalicular Cystskeleton With Special Reference to Actin and Actin-Binding Proteins," Hepatology, 1995, 21(4):1106-1113, 8 pgs.

The United States Pharmacopei: The National Formulary (USP 24 NF 19), United States Pharmacopeial Convention, Inc., Rockville, MD, 1999, 4 pgs., Table of Contents Only.
Van De Garde, M.D., et al., "Liver Monocytes and Kupffer Cells Remain Transcriptionally Distinct during Chronic Viral Infection," PLoS One, 2016, 11(11):e016694, 16 pgs.
Verma, S., et al., "Diagnosis, management and prevention of drug-induced liver injury," Gut, 2009, 58:1555-1564, 10 pgs.
Vosough, M., et al. "Generation of Functional Hepayocyte-Like Cells from Human Pluripotent Stem Cells in a Scalable Suspension Culture," Stem Cells Dev, 2013, 22(20):2693-2705, 13 pgs.
Wang, Y., et al., "Hepatic stellate cells, liver innate immunity, and hepatitis C virus," J Gastroenterol Hepatol, 2013, 28(Suppl 1):112-115, 8 pgs.
Warren, C.R., et al., "The NextGen Genetic Association Studies Consortium: A Foray into In Vitro Population Genetics," Cell Stem Cell, 2017, 20:431-433, 3 pgs.
Warren, C.R., et al., "Induced Pluripotent Stem Cell Differentiation Enables Functional Validation of GWAS Variant in Metabolic Disease," Cell Stem Cell, 2017, 20:547-557, 18 pgs.
Wells, J.M., et al., "Early mouse endoderm is patterned by soluble factors from adjacent germ layers," Development, 2000, 127:1563-1572, 10 pgs.
Woltjen, K., et al., "piggyBac transposition reprograms fibroblasts to induced pluripotent stem cells," Nature, 2009, 458(7239):766-770, 13 pgs.
Workman, M.J., et al., "Engineered human pluripotent-stem-cell-derived intestinal tissues with a functional enteric nervous system," Nat Med, 2017, 23(1):49-59, 29 pgs.
Xu, R., et al., "Association Between Patatin-Like Phospholipase Domain Containing 3 Gene (PNPLA3) Polymorphisms and Nonalcoholic Fatty Liver Disease: A HuGE Review and Meta-Analysis," Sci Rep, 2015, 5:9284, 11 pgs.
Yanagimachi, M.D., et al., "Robust and Highly-Efficient Differentiation of Functional Monocytic Cells from Human Pluripotent Stem Cells under Serum- and Feeder Cell-Free Conditions," PLoS One, 2013, 8(4):e59243, 9 pgs.
Yang, K., et al., "Systems Pharmacology Modeling Predicts Delayed Presentation and Species Differences in Bile Acid-Mediated Troglitazone Hepatotoxicity," Clin Pharmacol Ther, 2014, 96(5):589-598, 21 pgs.
Yoneda, M., et al., "Noninvasive assessment of liver fibrosis by measurement of sitffness in patients with nonalcoholic fatty liver disease (NAFLD)," Dig Liver Dis, 2008, 40:371-378, 8 pgs.
Zain, S.M., et al., "A common variant in the glucokinase regulatory gene rs780094 and risk of nonalcoholic fatty liver disease: A meta-analysis," J Gastroenterol Hepatol, 2015, 30:21-27, 7 pgs.
Zambrano, E., et al., "Total parenteral Nutrition Induced Pathology: An Autopsy Series of 24 Newborn Cases," Pediatr Dev Pathol, 2004, 7:425-432, 8 pgs.
Zabrowski, J., et al., "Induction of swelling of liver mitochondria by fatty acids of various chain length," Biochim Biophys Acta, 1963, 70:596-598, 3 pgs.
Zhou, H., et al., "Generation of Induced Pluripotent Stem Cells Using Recombinant Proteins," Cell Stem Cell, 2009, 4(5):381-384, 4 pgs.
Zorn, A.M., et al., "Vertebrate Endoderm Development and Organ Formation," Annu Rev Cell Dev Biol, 2009, 25:221-251, 36 pgs.
International Search Report and Written Opinion dated Jan. 19, 2018 for Application No. PCT/US2017/059845, 13 pgs.
International Search Report and Written Opinion dated Jan. 29, 2018 for Application No. PCT/US2017/059860, 13 pgs.
International Search Report and Written Opinion dated Jan. 18, 2018 for Application No. PCT/US2017/059865, 11 pgs.
U.S. Appl. No. 62/417,371, filed Nov. 4, 2016.
U.S. Appl. No. 62/517,414, filed Jun. 9, 2017.
U.S. Appl. No. 16/346,188, filed Apr. 30, 2019, by Takebe et al., Titled: Liver Organoid Compositions and Methods of Making and Using Same.
U.S. Appl. No. 16/346,188, filed Apr. 30, 2019, by Takebe et al., Titled: Liver Organoid Disease Models and Methods of Making and Using Same.

(56) References Cited

OTHER PUBLICATIONS

Adorini, L., et al., "Farnesoid X receptor targeting to treat nonalcoholic steatohepatitis," Drug Discovery Today, Sep. 2012, 17(17/18):988-997, 10 pgs.

Cincinnati Children's Hospital Medical Center, "Scientists grow human esophagus in lab: Tiny organoids enable personalized disease diagnosis, regenerative therapies," CCHMC Public Press Release, Sep. 20, 2018, 2 pgs.

Hardy, T., et al., "Nonalcoholic fatty liver disease: new treatments," Curr Opin Gastroenterol, May 2015, 31(3):175-183, 9 pgs.

Mudaliar, S., et al., "Efficacy and Safety of the Farnesoid X Receptor Agonist Obeticholic Acid in Patients with Type 2 Diabetes and Nonalcoholic Fatty Liver Disease," Gastroenterology, 2013, 145:574-582, 10 pgs.

Mullin, E., "Tiny Human Esophagus Grown in the Lab—Here's Why: Miniature version of the organ that guides food to the stomach could help scientists treat a variety of medical ailments," National Geographic, Sep. 20, 2018, downloaded from https://www.nationalgeographic.com/science/2018/news-human-esophagus-grown-lab-stem-cells-cancer-health.html, 5 pgs.

Sandoiu, A., "Scientists create human esophagus in stem cell first," Medical News Today, Sep. 21, 2018, downloades from https://www.medicalnewstoday.com/articles/323118.php, 4 pgs.

Schuppan, D., et al., "Non-alcoholic steatohepatitis: Pathogenesis and novel therepeutic approaches," Journal of Gastroenterology and Hepatology, 2013, 28(Suppl 1):68-76, 9 pgs Singh, S., et al., "Comparative Effectiveness of Pharmacological Interventions for Nonalcoholic Steatohepatitis: A Systematic Review and Network Meta-analysis," Hepatology, Nov. 2015, 62(5):1417-1432, 16 pgs.

\* cited by examiner

COMPOSITIONS AND METHODS OF TREATING LIVER DISEASE

CROSS REFERENCE TO RELATED APPLICATIONS

This application claims priority to and benefit of International Patent Application PCT/US17/59865, entitled "Compositions and Methods of Treating Liver Disease," filed Nov. 3, 2017, which claims priority to and benefit of U.S. Provisional Patent Application 62/417,371, filed Nov. 4, 2016, and 62/517,414, filed Jun. 9, 2017, the contents of each are incorporated by reference in their entirety for all purposes.

BACKGROUND

PNALD is the most devastating complication of long-term PN that occurs in the majority of children receiving PN (Kumar and Teckman, 2015; Orso et al., 2016; Zambrano et al., 2004). Because its progression is typically insidious and its long-term consequences are generally underappreciated, PNALD is often recognized too late, when liver injury is irreversible. It is histologically characterized by intrahepatic cholestasis but can progress to fibrosis and cirrhotic liver failure with continued exposure to PN. There are no established ameliorative strategies for PNALD and PNALD is the leading indication for liver transplantation in infants (El Kasmi et al., 2013).

BRIEF SUMMARY

Disclosed are methods of treating or reducing the occurrence of a steatohepatitis disorder. The disorder may include, for example, NASH, parenteral nutrition associated liver disease (PNALD), or genetic forms of liver disease. The method may comprise the step of administering a composition comprising obeticholic acid to an individual in need thereof.

BRIEF DESCRIPTION OF THE DRAWING

Those of skill in the art will understand that the drawings, described below, are for illustrative purposes only. The drawings are not intended to limit the scope of the present teachings in any way.

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
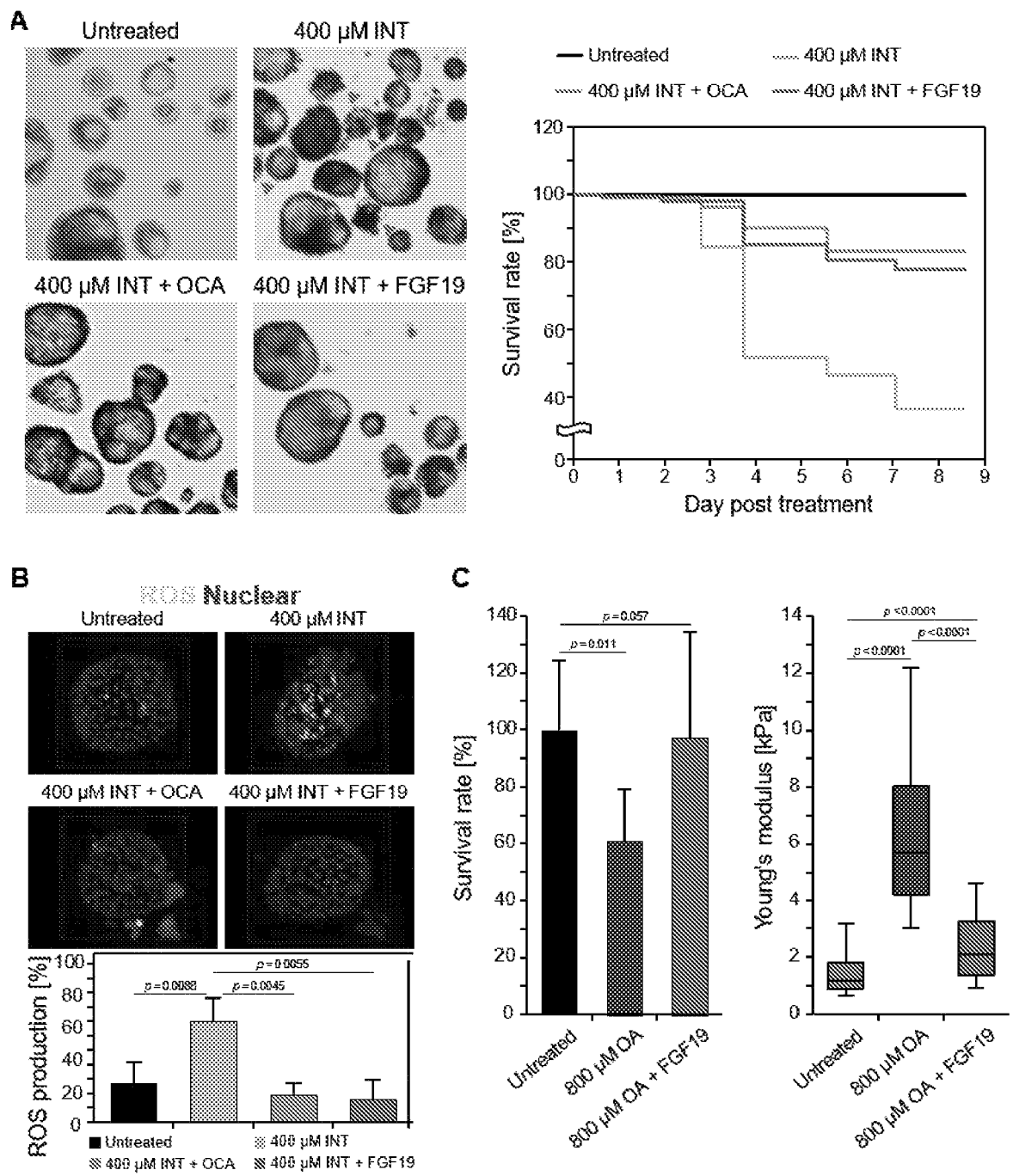
FIG. 1. Obeticholic acid treatment rescue PNALD like pathology in vitro A. Bright-field image of and survival rate (%) of HLO treated 0 (black line), 400 µM Intralipid (Int; light blue line), 400 µM Int with OCA (gray line), and 400 µM Int with 40 ng/ml FGF19 (pink line). Arrowheads indicate the dead organoids with clumped morphology in the images. Survival rate (%) of 0 (black bar), 800 µM OA (blue bar), 800 µM OA+FGF19 (pink bar) at the same time point. The survival of 800 µM OA HLO was significantly improved by FGF19 addition. B. Live-cell imaging of ROS (green) and nuclear (blue). OCA (gray bar) and FGF19 (pink bar) inhibit the ROS production caused by 400 µM Int (light blue bar). C. Intralipid. The stiffness of 0 (gray bar), 800 µM OA (blue bar), 800 µM OA+FGF19 (pink bar) treated HLO was assessed by AFM. The stiffness of 800 µM OA HLO was significantly softened by FGF19 addition.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms refer to children.

"Therapeutically effective amount" relates to the amount or dose of an active compound or composition described herein that will lead to one or more therapeutic effect, in particular, a desired beneficial effect. A therapeutically effective amount of a substance can vary according to factors such as the disease state, age, sex, and weight of the subject, and the ability of the substance to elicit a desired response in the subject. Dosage regime may be adjusted to provide the optimum therapeutic response. For example, several divided doses may be administered daily or the dose may be proportionally reduced as indicated by the exigencies of the therapeutic situation.

The term "parenteral nutrition," or "intravenous feeding," is a method of providing nutrition into an individual via intravenous administration. Depending on which vein is used, this procedure is often referred to as either total parenteral nutrition (TPN) or peripheral parenteral nutrition (PPN).

The phrase "pharmaceutically acceptable," as used in connection with compositions of the disclosure, refers to molecular entities and other ingredients of such compositions that are physiologically tolerable and do not typically produce untoward reactions when administered to a subject (e.g., human). In certain embodiments, as used herein, the term "pharmaceutically acceptable" means approved by a regulatory agency of a Federal or a state government or listed in the U.S. Pharmacopeia or other generally recognized pharmacopeia for use in mammals (e.g., humans).

The terms "pharmaceutically acceptable salts" or "a pharmaceutically acceptable salt thereof" refer to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts; salts of free acids and bases; inorganic salts, e.g., sulfate, hydrochloride, and hydrobromide; and other salts which are currently in widespread pharmaceutical use and are listed in sources well known to those of skill in the art, such as The Merck Index. Any suitable constituent can be selected to make a salt of an active drug discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives of the disclosed actives can also be suitable for use in the compositions and methods disclosed herein. A salt of a compound of this disclosure may be formed between an acid and a basic group of the compound, such as an amino functional group, or a base and an acidic group of the compound, such as a carboxyl functional group. According to another embodiment, the compound is a pharmaceutically acceptable acid addition salt. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The term "carrier" applied to pharmaceutical compositions of the disclosure refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are described in "Remington's Pharmaceutical Sciences" (any edition).

The term "compound," as used herein, is also intended to include any salts, solvates, or hydrates thereof.

Applicant has discovered novel methods for the treatment of liver disease in an individual in need thereof, which may include administration of a disclosed compound to an individual in need thereof.

In one aspect, a method of treating or reducing the occurrence of a steatohepatitis disorder is disclosed. The disorder may include, for example, NASH, parenteral nutrition associated liver disease (PNALD), or genetic forms of liver disease. The method may comprise the step of administering a composition comprising obeticholic acid to an individual in need thereof.

In one aspect, the composition may be administered in an amount sufficient to reduce or prevent the occurrence of liver cell fibrosis.

In one aspect, the composition may be administered prior to, following, or during administration of parenteral nutrition to said individual in need thereof.

In one aspect, a composition is disclosed, wherein the composition may comprise total parenteral nutrition (TPN) composition or peripheral parenteral nutrition (PPN) composition; and obeticholic acid.

In a further aspect, an article of manufacture is disclosed. The article of manufacture may comprise a container, a composition as described herein, the composition being in a dosage form, and instructions for administering the dosage form to an individual diagnosed or suspected of having or developing a liver disease as disclosed herein.

Dosage

In one aspect, an agent disclosed herein may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of the composition.

The compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, intralesional, or intramuscular forms all utilizing dosage forms well known to those of ordinary skill in the pharmaceutical arts. The compositions may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen.

In one aspect, the compounds may be administered at the rate of 100 μg to 1000 mg per day per kg of body weight. Orally, the compounds may be suitably administered at the rate of about 100, 150, 200, 250, 300, 350, 400, 450, or 500 μg to about 1, 5, 10, 25, 50, 75, 100, 200, 300, 400, 500, 600, 700, 800, 900, 1000 mg per day per kg of body weight. The required dose can be administered in one or more portions. For oral administration, suitable forms are, for example, tablets, gel, aerosols, pills, dragees, syrups, suspensions, emulsions, solutions, powders and granules; one method of administration includes using a suitable form containing from 1 mg to about 500 mg of active substance. In one aspect, administration may comprise using a suitable form containing from about 1, 2, 5, 10, 25, or 50 mg to about 100, 200, 300, 400, 500 mg of active substance.

A dosage regimen will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount of a drug required to prevent, counter, or arrest progression of a symptom or effect of a muscle contracture can be readily determined by an ordinarily skilled physician The pharmaceutical compositions may include suitable dosage forms for oral, parenteral (including subcutaneous, intramuscular, intradermal and intravenous), transdermal, sublingual, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are generally known in the art. The pharmaceutical compositions are prepared by conventional techniques appropriate to the desired preparation containing appropriate amounts of the active ingredient, that is, one or more of the disclosed active agents or a pharmaceutically acceptable salt thereof according to the invention.

The dosage of an agent disclosed herein used to achieve a therapeutic effect will depend not only on such factors as the age, weight and sex of the patient and mode of administration, but also on the degree of inhibition desired and the potency of an agent disclosed herein for the particular disorder or disease concerned. It is also contemplated that the treatment and dosage of an agent disclosed herein may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

Routes of Administration

Any suitable route of administration can be employed for providing the patient with an effective dosage of the disclosed compositions. For example, oral, rectal, transdermal, parenteral (subcutaneous, intramuscular, intravenous), intrathecal, topical, inhalable, and like forms of administration can be employed. Suitable dosage forms include tablets, troches, dispersions, suspensions, solutions, capsules, patches, and the like. Administration of medicaments prepared from the compounds described herein can be by any suitable method capable of introducing the compounds into the bloodstream. In some embodiments, the formulations can contain a mixture of active compounds with pharmaceutically acceptable carriers or diluents known to those of skill in the art.

The compositions can be prepared in any desired form, for example, tables, powders, capsules, injectables, suspensions, sachets, cachets, patches, solutions, elixirs, and aerosols. Carriers such as starches, sugars, microcrystalline cellulose, diluents, granulating agents, lubricants, binders, disintegrating agents, and the like can be used in oral solid preparations. In certain embodiments, the compositions are prepared as oral solid preparations (such as powders, capsules, and tablets). In certain embodiments, the compositions are prepared as oral liquid preparations. In some embodiments, the oral solid preparations are tablets. If desired, tablets can be coated by standard aqueous or non-aqueous techniques.

In addition to the dosage forms set out above, one or more disclosed compounds may also be administered by sustained release, delayed release, or controlled release compositions and/or delivery devices.

Pharmaceutical compositions suitable for oral administration can be provided as discrete units such as capsules, cachets, sachets, patches, injectables, tablets, and aerosol sprays, each containing predetermined amounts of the active ingredients, as powder or granules, or as a solution or a suspension in an aqueous liquid, a non-aqueous liquid, an oil-in-water emulsion, or a water-in-oil liquid emulsion. Such compositions can be prepared by any of the conventional methods of pharmacy, and may include the step of bringing into association the active ingredients with a carrier which constitutes one or more ingredients. In general, the compositions may be prepared by uniformly and intimately admixing the active ingredients with liquid carriers, finely divided solid carriers, or both, and then, optionally, shaping the product into the desired presentation.

For example, a tablet can be prepared by compression or molding, optionally, with one or more additional ingredients. Compressed tablets can be prepared by compressing in a suitable machine the active ingredient in a free-flowing form such as powder or granules, optionally mixed with a binder, lubricant, inert diluent, surface active or dispersing agent. Molded tablets can be made by molding, in a suitable machine, a mixture of the powdered compound moistened with an inert liquid diluent.

A composition or formulation may be administered to a subject continuously or periodically.

The compositions or fractions thereof typically comprise suitable pharmaceutical diluents, excipients, vehicles, or carriers selected based on the intended form of administration, and consistent with conventional pharmaceutical practices. The carriers, vehicles etc. may be adapted to provide an additive, synergistically effective or therapeutically effective amount of the active compounds. Suitable pharmaceutical diluents, excipients, vehicles, and carriers are described in the standard text, Remington: The Science and Practice of Pharmacy, and in The United States Pharmacopeia: The National Formulary (USP 24 NF 19) published in 1999. By way of example, for oral administration in the form of a capsule or tablet, the active components can be combined with an oral, non-toxic pharmaceutically acceptable inert carrier such as lactose, starch, sucrose, methyl cellulose, magnesium stearate, glucose, calcium, sulfate, dicalcium phosphate, mannitol, sorbital, and the like. For oral administration in a liquid form, the agents may be combined with any oral, non-toxic, pharmaceutically acceptable inert carrier such as ethanol, glycerol, water, and the like. Suitable binders (e.g. gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof.

In one aspect, a pharmaceutical composition may have pH from about 7 to 10.

Formulations for parenteral administration of a composition may include aqueous solutions, syrups, aqueous or oil suspensions and emulsions with edible oil such as cottonseed oil, coconut oil or peanut oil. Dispersing or suspending agents that can be used for aqueous suspensions include synthetic or natural gums, such as tragacanth, alginate, acacia, dextran, sodium carboxymethylcellulose, gelatin, methylcellulose, and polyvinylpyrrolidone.

Compositions for parenteral administration may include sterile aqueous or non-aqueous solvents, such as water, isotonic saline, isotonic glucose solution, buffer solution, or other solvents conveniently used for parenteral administration of therapeutically active agents. A composition intended for parenteral administration may also include conventional additives such as stabilizers, buffers, or preservatives.

In an embodiment, a solid form pharmaceutical composition is provided (e.g. tablets, capsules, powdered, or pulverized form) comprising one or more disclosed compounds or salt thereof.

After pharmaceutical compositions have been prepared, they can be placed in an appropriate container and labeled for treatment of an indicated condition. For administration of a composition, such labeling would include amount, frequency, and method of administration.

Kits

Kits are also provided. In one aspect, a kit may comprise or consist essentially of agents or compositions described herein. The kit may be a package that houses a container which may contain a composition comprising an oxime or pharmaceutically acceptable salt thereof as disclosed herein, and also houses instructions for administering the agent or composition to a subject. In one aspect, a pharmaceutical pack or kit is provided comprising one or more containers filled with one or more composition as disclosed herein. Associated with such container(s) can be various written materials such as instructions for use, or a notice in the form prescribed by a governmental agency regulating the manufacture, use or sale of pharmaceuticals or biological products, which notice reflects approval by the agency of manufacture, use, or sale for human administration.

As there may be advantages to mixing a component of a composition described herein and a pharmaceutically acceptable carrier, excipient or vehicle near the time of use, kits in which components of the compositions are packaged separately are disclosed. For example, the kit can contain an active ingredient in a powdered or other dry form in, for example, a sterile vial or ampule and, in a separate container within the kit, a carrier, excipient, or vehicle, or a component of a carrier, excipient, or vehicle (in liquid or dry form). In one aspect, the kit can contain a component in a dry form, typically as a powder, often in a lyophilized form in, for example, a sterile vial or ampule and, in a separate container within the kit, a carrier, excipient, or vehicle, or a component of a carrier, excipient, or vehicle. Alternatively, the kit may contain a component in the form of a concentrated solution that is diluted prior to administration. Any of the components described herein, any of the carriers, excipients or vehicles described herein, and any combination of components and carriers, excipients or vehicles can be included in a kit.

Optionally, a kit may also contain instructions for preparation or use (e.g., written instructions printed on the outer container or on a leaflet placed therein) and one or more devices to aid the preparation of the solution and/or its administration to a patient (e.g., one or a plurality of syringes, needles, filters, tape, tubing, alcohol swabs, or the like). Compositions which are more concentrated than those administered to a subject can be prepared. Accordingly, such compositions can be included in the kits with, optionally, suitable materials (e.g., water, saline, or other physiologically acceptable solutions) for dilution. Instructions included with the kit can include, where appropriate, instructions for dilution.

In other embodiments, the kits can include pre-mixed compositions and instructions for solubilizing any precipitate that may have formed during shipping or storage. Kits containing solutions of one or more of the aforementioned active agents, or pharmaceutically acceptable salts thereof, and one or more carriers, excipients or vehicles may also contain any of the materials mentioned above (e.g., any device to aid in preparing the composition for administration or in the administration per se). The instructions in these kits may describe suitable indications (e.g., a description of patients amenable to treatment) and instructions for administering the solution to a patient.

EXAMPLES

Repurposing OCA for PNALD Therapy

In this study, Applicant found that OCA and FGF19 inhibited ROS production caused by Intralipid exposure in HLO, leading to an improvement in survival rate of HLO. Moreover, the stiffness of OA treated HLO, measured by AFM, was decreased by FGF19 exposure. These results provide direct experimental evidence that OCA and FGF19 play a preventive role in the pathogenesis of PNALD organoid model and that the suppression of ROS production and fibrosis by FXR agonism is the likely mechanism of protection against PNALD. Our study thus highlighted the potential repurposing of OCA for the treatment of patients with PNALD.

Obeticholic acid treatment improved PNALD-like pathology of HLO

Figure 2:
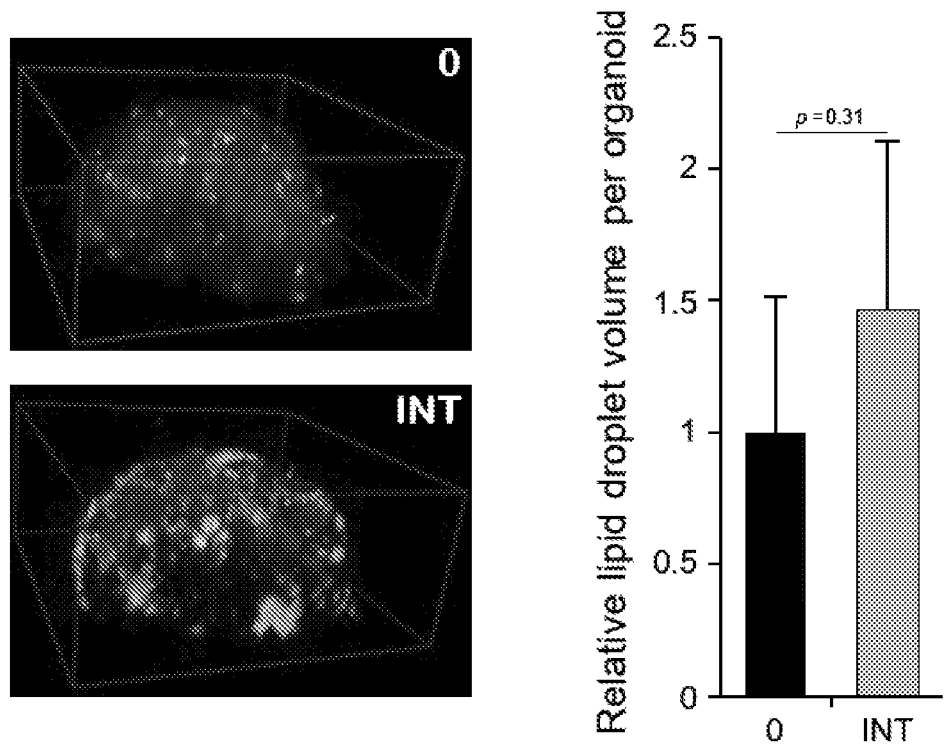
FIG. 2. Lipids accumulation in the organoid in the presence and absence of 400 µM Intralipid FIG. 3. Bright-field image of liver organoids in the culture of non-treatment, 800 µM of OA alone, and 800 µM of OA with 40 ng/ml FGF19.
Figure 3:
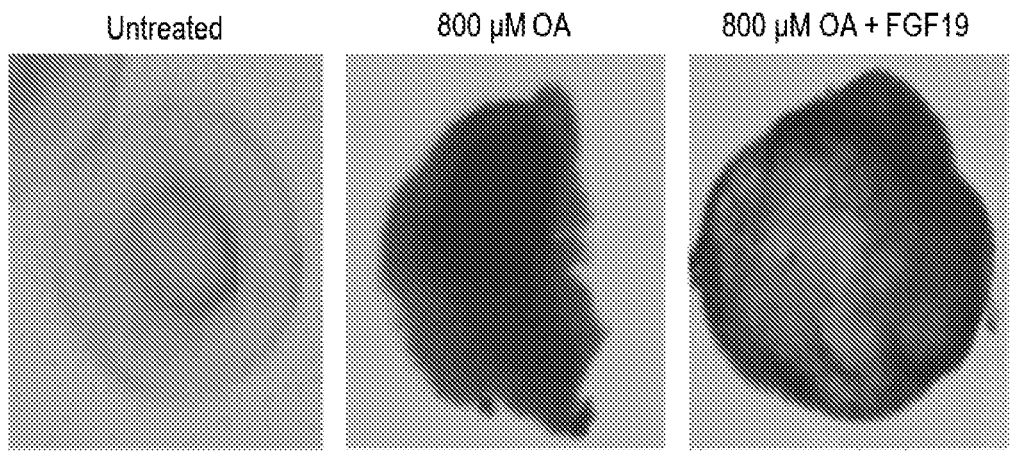

PNALD is an iatrogenic fatty liver disease which occurs frequently in infants provided with parental nutrition (PN) solutions employing a lipid emulsion (Intralipid) that provide life-sustaining calories in the setting of inadequate absorption of enteral nutrients (Kumar and Teckman, 2015; Orso et al., 2016). PNALD has a histological evidence of steatosis, cell death (apoptosis), and fibrosis (Nandivada et al., 2013). To recapitulate PNALD pathology in HLO, we reconstituted components of Intralipid and placed it directly into HLO culture. Similar to OA treatment, significant lipid accumulation was confirmed in 400 µM Intralipid treated HLO reflecting a steatosis-like condition (FIG. 2). In parallel, we established an organoid survival assessment algorithm by morphological analysis backed by viability assessment (FIGS. 3 and 2, panel A.) and demonstrated that HLO survival of 400 µM Intralipid treated group was severely compromised by 37% after 12 days of culture (FIG. 2, panel A).

Because there are no established ameliorative strategies, and PNALD is the leading indication for liver transplantation in infants (El Kasmi et al., 2013), we further investigated preventive and therapeutic effects of FXR agonist obeticholic acid (OCA) and FGF19 hormone that are activated by OCA, which have shown great potential in nonalcoholic steatohepatitis treatment (Dash et al., 2017; Kumar and Teckman, 2015; Neuschwander-Tetri et al., 2015). To implicate the therapeutic significance of OCA and FGF19 for PNALD like pathology in HLO, OCA and FGF19 were added to 400 µM Intralipid exposed HLO. By addition of OCA and FGF19 into PNALD-HLO, the number of surviving organoids remarkably improved around 83 and 78% in total, respectively. Mechanistically, the accumulation of reactive oxygen species (ROS) is strongly associated with the fatty liver related hepatocyte death (Nandivada et al., 2013; Tsedensodnom and Sadler, 2013). We thus wondered whether OCA and FGF19 would inhibit the production of ROS so we sought to confirm that theory with live-cell imaging with CellROX dye. Consistent with HLO survival improvements, ROS production was 60% in 400 µM Intralipid treated HLO but reduced to 20 and 30% by OCA and FGF19 treatments, respectively (FIG. 7, B), suggesting that OCA and FGF19 might have therapeutic potential against PNALD through suppressing ROS production.

To further determine whether OCA and FGF19 have an impact on fibrosis, HLO stiffness was assessed. Organoid damage induced by Intralipid is extremely significant and treated HLOs for 5 days are not able to be stabilized on a dish, which is a minimal requirement for assessing the rigidity by AFM. To circumvent this limitation, the stiffness was assessed at Day3. These observations indicate that OCA and FGF19 reduce the progression of fibrosis, potentially alleviating PNALD phenotype in an organoid.

METHODS hPSCs Maintenance. The TkDA3 human iPSC clone used in this study was kindly provided by K. Eto and H. Nakauchi. Human iPSC lines were maintained as described previously (Takebe et al., 2015; Takebe et al., 2014). Undifferentiated hiPSCs were maintained on feeder-free conditions in mTeSR1 medium (StemCell technologies, Vancouver, Canada) on plates coated with Matrigel (Corning Inc., NY, USA) at 1/30 dilution at 37° C. in 5% $CO_2$ with 95% air.

Definitive endoderm induction. Human iPSCs into definitive endoderm was differentiated using previously described methods with slight modifications (Spence et al., 2011). In brief, colonies of human iPSCs were isolated in Accutase (Thermo Fisher Scientific Inc., MA, USA) and 150,000 cells/mL were plated on Matrigel coated tissue culture plate (VWR Scientific Products, West Chester, Pa.). Medium was changed to RPMI 1640 medium (Life Technologies) containing 100 ng/mL Activin A (R&D Systems, MN, USA) and 50 ng/mL bone morphogenetic protein 4 (BMP4; R&D Systems) at day 1, 100 ng/mL Activin A and 0.2% fetal calf serum (FCS; Thermo Fisher Scientific Inc.) at day 2 and 100 ng/mL Activin A and 2% FCS at day 3. Day 4-6 cells were cultured in Advanced DMEM/F12 (Thermo Fisher Scientific Inc.) with B27 (Life Technologies) and N2 (Gibco, Calif., USA) containing 500 ng/ml fibroblast growth factor (FGF4; R&D Systems) and 3 uM CHIR99021 (Stemgent, MA, USA). Cells were maintained at 37° C. in 5% $CO_2$ with 95% air and the medium was replaced every day. Spheroids appeared on the plate at day 7 of differentiation.

HLO induction. At day 7, spheroids and attached cells are gently pipetted to be delaminated from dishes. They were centrifuged at 800 rpm for 3 minutes, embedded in a 100% Matrigel drop on the dishes in Advanced DMEM/F12 with B27, N2 and 2 uM retinoic acid (RA; Sigma, MO, USA) after removing supernatant, and cultured for 4 days. After RA treatment, spheroids embedded in the Matrigel drop were cultured in Hepatocytes Culture Medium (HCM; Lonza, MD, USA) with 10 ng/mL hepatocyte growth factor (HGF; PeproTech, NJ, USA), 0.1 uM Dexamethasone (Dex; Sigma) and 20 ng/mL Oncostatin M (OSM; R&D Systems). Cultures for HLO induction were maintained at 37° C. in 5% $CO_2$ with 95% air and the medium was replaced every 2-3 days. To analyze HLO (day 20-30), organoids were isolated from Matrigel by scratching and pipetting.

Albumin, IL-6, and P3NP ELISA. To measure albumin secretion level of HLO, 200 µL of culture supernatant was collected from HLO embedded in Matrigel. For IL-6 and P3NP, 20-30 organoids were seeded and cultured on an ultra-low attachment multiwell plates 96 well plate (Corning). To define the exact number of organoids in each well and lastly normalize the secreted level for IL-6 and P3NP by the number, the organoids were captured on The KEYENCE BZ-X710 Fluorescence Microscope. The culture supernatants were collected at 24 hrs (for albumin), 96 hrs (for IL-6) and 120 hrs (P3NP) time points after the culture and stored at −80° C. until use. The supernatant was centrifuged at 1,500 rpm for 3 min and to pellet debris, and the resulting supernatant was assayed with Human Albumin ELISA Quantitation Set (Bethyl Laboratories, Inc., TX, USA), Human IL-6 ELISA Kit (Biolegend, CA, USA), and Human N-terminal procollagen III propeptide, PIIINP ELISA Kit (My BioSource, CA, USA) according to the manufacturer's instructions. Significance testing was conducted by Student's t-test.

Bile transport activity. Fluorescein diacetate was used for evaluating bile transport activity in organoids. 10 mg/mL fluorescein diacetate (Sigma) was added into HCM media cultured with HLO and allowed to sit for 5 minutes and captured using fluorescent microscopy BZ-X710 (Keyence, Osaka, Japan).

Phagocyte, lipids, ROS live-cell imaging. After being cultured in an ultra-low attachment 6 multi-well plate, 5-10 HLO were picked up and seeded in a Microslide 8 Well Glass Bottom plate (Ibidi, WI, USA) and subjected to live-cell staining. The following antibodies were used: pHrodo® Red S. aureus Bioparticles® Conjugate for Phagocyte activity (Thermo Fisher Scientific Inc.), BODIPY® 493/503 for lipids (Thermo Fisher Scientific Inc.), Di-8-ANEPPS for membrane (Thermo Fisher Scientific Inc.), and CellROX green reagent for ROS detection (Thermo Fisher Scientific Inc.). Nuclear staining was marked by NucBlue Live ReadyProbes Reagent (Thermo Fisher Scientific Inc.). HLO was visualized and scanned on a Nikon A1 Inverted Confocal Microscope (Japan) using 60× water immersion objectives. The final lipid droplet volume was calculated by IMARIS8 and normalized by each organoid size. Significance testing for lipid droplet volume and ROS production (%) was conducted by Student's t-test.

HE staining and immunohistochemistry. HLO were isolated from Matrigel and fixed in 4% paraformaldehyde and embedded in paraffin. Sections were subjected to HE and immunohistochemical staining The following primary antibodies were used: anti-alpha smooth muscle actin antibody (1:200 dilution; abcam, Cambridge, UK), Desmin antibody (Pre-diluted; Roche, Basel, Switzerland), and CD68 antibody (1:200 dilution; abcam).

Flow cytometry. HLO were isolated from 10 Matrigel droplets and washed by 1×PBS. HLO were dissociated to single cells by the treatment of Trypsin-EDTA (0.05%), phenol red (Gibco) for 10 min After PBS wash, the single cells were subjected to flow cytometry with BV421-conjugated Epcam antibody (BioLegend), PE-conjugated CD166 antibody (eBioscience, CA, USA), and PE/Cy7-CD68 (eBioscience). DNA was measured by propidium iodide staining.

LPS and FFA exposure and OCA and FGF19 treatment. 20-30 hLOHLO, which had been isolated from Matrigel and washed by 1×PBS, were divided into each condition and cultured on an ultra-low attachment 6 multi-well plates (Corning). HLO were cultured with LPS (Sigma), OA (Sigma), LA (Sigma), SA (Sigma), or PA (Sigma) and collected at day 1 and 3 (for LPS HLO) and at day 3 and 5 (for OA) after the culture. To test the inhibitory effect of OCA (INT-747, MedChem Express, NJ, USA) and human FGF19 recombinant (Sigma) on HLO, 20-30 HLO were cultured in HCM media in the presence or absence of oleic acid (800 $\mu$M), and 1 $\mu$M OCA and 40 ng/ml FGF19 were added into 800 $\mu$M OA condition. HLO were collected at day 3 for lipids live-cell imaging and at day 5 for stiffness measurement.

Whole mount immunofluorescence. HLO were fixed for 30 min in 4% paraformaldehyde and permeabilized for 15 min with 0.5% Nonidet P-40. HLO were washed by 1×PBS three times and incubated with blocking buffer for 1 h at room temperature. HLO were then incubated with primary antibody; anti-alpha smooth muscle actin antibody (1:50 dilution; abcam) overnight at 4° C. HLO were washed by 1×PBS and incubated in secondary antibody in blocking buffer for 30 min at room temperature. HLO were washed and mounted using Fluoroshield mounting medium with DAPI (abcam). The stained HLO were visualized and scanned on a Nikon A1 Inverted Confocal Microscope (Japan) using 60× water immersion objectives.

RNA isolation, RT-qPCR. RNA was isolated using the RNeasy mini kit (Qiagen, Hilden, Germany). Reverse transcription was carried out using the SuperScriptIII First-Strand Synthesis System for RT-PCR (Invitrogen, CA, USA) according to manufacturer's protocol. qPCR was carried out using TaqMan gene expression master mix (Applied Biosystems) on a QuantStudio 3 Real-Time PCR System (Thermo Fisher Scientific Inc.). All primers and probe information for each target gene was obtained from the Universal ProbeLibrary Assay Design Center (https://qpcr.probefinder.com/organism.jsp). Significance testing was conducted by Student's t-test.

HLO stiffness measurement by AFM. HLOs treated with 0, 50200, 1400, 2800 ng/mL$\mu$M LPSOA were used for stiffness measurement with a AFM (NanoWizard IV, JPK Instruments, Germany). The AFM head with a silicon nitride cantilever (CSC37, k=0.3 N/m, MikroMasch, Bulgaria) was mounted on a fluorescence stereo microscope (M205 FA, Leica, Germany) coupled with a Z-axis piezo stage (JPK CellHesion module, JPK Instruments, Germany), which allows the indentation measurement up to the depth of ~100 $\mu$m. As a substrate for organoids, a fibronectin-coated dish was used. The tissue culture dish ($\varphi$=34 mm, TPP Techno Plastic Products, Switzerland) was first incubated with a 1 $\mu$g/mL fibronectin solution (Sigma)) at 4° C. for overnight. Then, the tissue culture dish was washed twice by distilled water and dried for 1 hour. Thereafter, HLOs incubated with OALPS for 51 days were deposited to the fibronectin-coated dish and incubated for 1 hour at 37° C. The sample dish was then placed onto the AFM stage, and force-distance curves in a 14×14 matrix in a 25×25 $\mu$m square were measured from each HLO. Finally, Young's moduli (E, Pa) of HLOs were determined by fitting the obtained force-distance curves with the modified Hertz model (Sneddon, 1965). Dunn-Holland-Wolfe test was performed for significance testings.

THP-1 cell migration assay. THP-1 cell, which was gifted from T. Suzuki, was maintained in Advanced DMEM/F12 (Thermo Fisher Scientific Inc.) containing 10% FBS. THP-1 floating cells were collected, and 200,000 cells were added with serum-free Advanced DMEM/F12 to the membrane chamber of the CytoSelect™ 96-Well Cell Migration Assay (5 $\mu$m, Fluorometric Format; Cell Biolabs, CA, USA). 10-20 HLO were cultured in HCM media including 0, 400, 800 $\mu$M OA with an ultra-low attachment 96 multi-well plate (Corning) for three days. To define the exact number of organoids in each well and lastly normalize the final migrated cells by the number, the organoids were captured on The KEYENCE BZ-X710 Fluorescence Microscope. 150 $\mu$L of culture supernatant of HLO was collected and added to the feeder tray of the kit. The kit was incubated at 37° C. for 24 h in a 5% $CO_2$ cell culture incubator. Cells that had migrated were counted using Countess II FL Automated Cell Counter (Thermo Fisher Scientific Inc.). Significance testing was conducted by Student's t-test.

Triglyceride assay. For quantitative determination of triglycerides, HLO were isolated from one Matrigel drop and divided into HCM media in the presence or absence of oleic acid (800 μM). They were cultured on an ultra-Low attachment 6 multi-well plate for three days. Quantitative estimation of hepatic triglyceride accumulation was performed by an enzymatic assay of triglyceride mass using the EnzyChrom Triglyceride assay kit (Bioassay Systems, CA, USA).

HLO survival assay. HLO were collected from Matrigel and washed by 1×PBS. 30-40 organoids were cultured on an ultra-low attachment 6 multi-well plate (Corning). HLO were captured on The KEYENCE BZ-X710 Fluorescence Microscope every day. The surviving and dead organoids were counted manually from the photo. HLO with a rounded configuration was counted as the surviving while the organoids with out of shape is counted as dead. To assess the survival rate of OA treated HLO at the same time point, 3D cell titer glo assay was used (Promega, Wi, USA).

Statistics and reproducibility. Statistical analysis was performed using unpaired two-tailed Student's t-test, Dunn-Holland-Wolfe test, or Welch's t-test. Results were shown mean±s.e.m.; P values <0.05 were considered statistically significant. N-value refers to biologically independent replicates, unless noted otherwise.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating or reducing the occurrence of a steatohepatitis disorder selected from NASH, parenteral nutrition associated liver disease (PNALD), and a genetic liver disease, comprising the step of administering a composition comprising obeticholic acid and Fibroblast Growth Factor 19 ("FGF19") to an individual in need thereof.

2. The method of claim 1, wherein said composition is administered in an amount sufficient to reduce the occurrence of liver cell fibrosis.

3. The method of claim 1 wherein said composition is administered prior to, following, or during administration of parenteral nutrition to said individual in need thereof.

4. The method of claim 1 wherein said composition comprises a buffer.

5. The method of claim 1 wherein said composition a carrier.

6. The method of claim 1 wherein said composition is administered parenterally or intravenously.

7. A composition comprising
   a. total parenteral nutrition (TPN) or peripheral parenteral nutrition (PPN);
   b. Fibroblast Growth Factor 19 ("FGF19"); and
   c. obeticholic acid.

8. An article of manufacture comprising a container, a composition of claim 7 in a dosage form, and instructions for administering said dosage form to an individual diagnosed or suspected of having or developing PNALD.

* * * * *

UNITED STATES PATENT AND TRADEMARK OFFICE
CERTIFICATE OF CORRECTION

PATENT NO. : 10,668,108 B2
APPLICATION NO. : 16/343157
DATED : June 2, 2020
INVENTOR(S) : Takanori Takebe et al.

It is certified that error appears in the above-identified patent and that said Letters Patent is hereby corrected as shown below:

On the Title Page

Column 1, Item (60), Line 1, under Related U.S. Application Data, delete "62/517,525," and insert --62/517,414,--.

On Page 2, Column 1, Item (56), Line 17, under Other Publications, delete "hapatocyte" and insert --hepatocyte--.

On Page 2, Column 1, Item (56), Line 18, under Other Publications, delete "cultue,"" and insert --culture,"--.

On Page 2, Column 1, Item (56), Line 23, under Other Publications, delete "Inducd" and insert --Induced--.

On Page 2, Column 1, Item (56), Line 30, under Other Publications, delete "Parental" and insert --Parenteral--.

On Page 2, Column 1, Item (56), Line 36, under Other Publications, delete "hepati" and insert --hepatic--.

On Page 2, Column 1, Item (56), Line 50, under Other Publications, delete "indocrine" and insert --endocrine--.

On Page 2, Column 2, Item (56), Line 9, under Other Publications, delete "pgs" and insert --pgs.--.

On Page 2, Column 2, Item (56), Line 15, under Other Publications, delete "200," and insert --2002,--.

On Page 3, Column 1, Item (56), Line 8, under Other Publications, delete "Effux" and insert --Efflux--.

Signed and Sealed this
Thirtieth Day of November, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,668,108 B2

On Page 3, Column 1, Item (56), Line 14, under Other Publications, delete "reeneration,"" and insert --regeneration,"--.

On Page 3, Column 1, Item (56), Line 33, under Other Publications, delete "expresssion" and insert --expression--.

On Page 3, Column 1, Item (56), Line 45, under Other Publications, delete "Differenced" and insert --Differences--.

On Page 3, Column 1, Item (56), Line 46, under Other Publications, delete "Hepatotocity," and insert --Hepatotoxicity,--.

On Page 3, Column 1, Item (56), Line 55, under Other Publications, delete "cellolose" and insert --cellulose--.

On Page 3, Column 1, Item (56), Line 65, under Other Publications, delete "K. W.," and insert --K.W.,--.

On Page 3, Column 1, Item (56), Line 66, under Other Publications, delete "specifications" and insert --specification--.

On Page 3, Column 2, Item (56), Line 1, under Other Publications, delete "canenin" and insert --catenin--.

On Page 3, Column 2, Item (56), Line 5, under Other Publications, delete "Compound" and insert --Compounded--.

On Page 3, Column 2, Item (56), Line 6, under Other Publications, delete "Retrospetive" and insert --Retrospective--.

On Page 3, Column 2, Item (56), Line 9, under Other Publications, delete "of" and insert --to--.

On Page 3, Column 2, Item (56), Line 15, under Other Publications, delete ""Comparison" and insert --"Comparison of--.

On Page 3, Column 2, Item (56), Line 17, under Other Publications, delete "355," and insert --322,--.

On Page 3, Column 2, Item (56), Line 21, under Other Publications, delete "Hepatotoxity," and insert --Hepatotoxicity,--.

On Page 3, Column 2, Item (56), Line 21, under Other Publications, delete "Engl" and insert --Engl j--.

On Page 3, Column 2, Item (56), Line 27, under Other Publications, delete "steatophepatitis" and insert --steatohepatitis--.

CERTIFICATE OF CORRECTION (continued)
U.S. Pat. No. 10,668,108 B2

On Page 3, Column 2, Item (56), Line 28, under Other Publications, delete "radomised," and insert --randomised,--.

On Page 3, Column 2, Item (56), Line 31, under Other Publications, delete "capcitis:" and insert --capacities:--.

On Page 3, Column 2, Item (56), Line 34, under Other Publications, delete "acis" and insert --acid--.

On Page 3, Column 2, Item (56), Line 46, under Other Publications, delete "Neurogeneis," and insert --Neurogenesis,--.

On Page 3, Column 2, Item (56), Line 48, under Other Publications, delete "D.," and insert --D., et al.,--.

On Page 3, Column 2, Item (56), Line 52, under Other Publications, delete "Berling," and insert --berlin--.

On Page 3, Column 2, Item (56), Line 64, under Other Publications, delete "PloS" and insert --PLoS--.

On Page 4, Column 1, Item (56), Line 13, under Other Publications, delete "Cell" and insert --Cells--.

On Page 4, Column 1, Item (56), Line 13, under Other Publications, delete "Pluripoent" and insert --Pluripotent--.

On Page 4, Column 1, Item (56), Line 52, under Other Publications, delete "vasularized" and insert --vascularized--.

On Page 4, Column 1, Item (56), Line 56, under Other Publications, delete "1148," and insert --1147,--.

On Page 4, Column 1, Item (56), Line 59, under Other Publications, delete "Interferring" and insert --Interfering--.

On Page 4, Column 1, Item (56), Line 67, under Other Publications, delete "Cystskeleton" and insert --Cytoskeleton--.

On Page 4, Column 2, Item (56), Line 1, under Other Publications, delete "Pharmacopei:" and insert --Pharmacopeia:--.

On Page 4, Column 2, Item (56), Line 6, under Other Publications, delete "016694," and insert --0166094,--.

On Page 4, Column 2, Item (56), Line 9, under Other Publications, delete "Hepayocyte" and insert --Hepatocyte--.

CERTIFICATE OF CORRECTION (continued)
U.S. Pat. No. 10,668,108 B2

On Page 4, Column 2, Item (56), Line 19, under Other Publications, delete "Variant" and insert --Variants--.

On Page 4, Column 2, Item (56), Line 42, under Other Publications, delete "sitffness" and insert --stiffness--.

On Page 4, Column 2, Item (56), Line 46, under Other Publications, delete "Gastoenterol" and insert --Gastroenterol--.

On Page 4, Column 2, Item (56), Line 47, under Other Publications, delete "Induced" and insert --Induced liver--.

On Page 4, Column 2, Item (56), Line 50, under Other Publications, delete "Zabrowski," and insert --Zbrowski,--.

On Page 5, Column 1, Item (56), Line 15, under Other Publications, delete "version" and insert --versions--.

On Page 5, Column 1, Item (56), Line 18, under Other Publications, delete "/2018" and insert --/2018/09--.

On Page 5, Column 1, Item (56), Line 21, under Other Publications, delete "downloades" and insert --downloaded--.

On Page 5, Column 1, Item (56), Line 24, under Other Publications, delete "therepeutic" and insert --therapeutic--.

In the Specification

In Column 1, Line 67, delete "intralipid" and insert --intralipid.--.

In Column 5, Line 38, delete "physician" and insert --physician.--.

In Column 10, Line 7, delete "Day3" and insert --Day 3--.

In Column 11, Line 36, delete "staining" and insert --staining.--.

In Column 11, Line 44, delete "min" and insert --min.--.

In Column 12, Line 35, delete "(Sigma))" and insert --(Sigma)--.